United States Patent
Sukavaneshvar et al.

(10) Patent No.: US 8,289,514 B2
(45) Date of Patent: Oct. 16, 2012

(54) SYSTEMS FOR MEASURING PROPERTIES OF A PHYSIOLOGICAL FLUID SUSPENSION

(75) Inventors: Sivaprasad Sukavaneshvar, Murray, UT (US); Edward R. Teitel, Houston, TX (US); Syed F. Mohammad, Salt Lake City, UT (US)

(73) Assignee: Aggredyne, Inc., Houston, TX (US)

( * ) Notice: Subject to any disclaimer, the term of this patent is extended or adjusted under 35 U.S.C. 154(b) by 346 days.

(21) Appl. No.: 12/398,480

(22) Filed: Mar. 5, 2009

(65) Prior Publication Data
US 2009/0225316 A1  Sep. 10, 2009

Related U.S. Application Data

(60) Provisional application No. 61/068,354, filed on Mar. 5, 2008.

(51) Int. Cl.
G01N 21/00 (2006.01)
(52) U.S. Cl. .................................. 356/337; 356/338
(58) Field of Classification Search .......... 356/335–343, 356/39–42, 426–428; 250/547, 222.2
See application file for complete search history.

(56) References Cited

U.S. PATENT DOCUMENTS

| | | | |
|---|---|---|---|
| 3,989,382 A | 11/1976 | Kent et al. | |
| 4,066,360 A | 1/1978 | Breddin et al. | |
| 4,135,818 A | 1/1979 | Kent et al. | |
| 4,284,412 A | 8/1981 | Hansen et al. | |
| 4,319,194 A | 3/1982 | Cardinal et al. | |
| 4,601,080 A | 7/1986 | Cook | |
| 4,936,674 A | 6/1990 | Ikeda et al. | |
| 5,061,381 A | 10/1991 | Burd | |
| 5,245,318 A * | 9/1993 | Tohge et al. | 340/611 |
| 5,293,210 A | 3/1994 | Berndt | |
| 5,325,295 A | 6/1994 | Fratantoni et al. | |
| 5,351,686 A | 10/1994 | Steuer et al. | |
| 5,352,413 A | 10/1994 | Kratzer et al. | |
| 5,372,136 A | 12/1994 | Steuer et al. | |
| 5,428,443 A | 6/1995 | Kitamura et al. | |
| 5,456,253 A | 10/1995 | Steuer et al. | |
| 5,523,238 A | 6/1996 | Varon et al. | |
| 5,563,041 A | 10/1996 | Reers | |
| 5,569,590 A | 10/1996 | Speck | |
| 5,796,480 A | 8/1998 | Igushi | |
| 5,907,399 A | 5/1999 | Shirasawa et al. | |

(Continued)

FOREIGN PATENT DOCUMENTS

JP   5-240863   9/1993

(Continued)

OTHER PUBLICATIONS

Hall et al., "Formulation of Occlusive Platelet Aggregats in Whole Blood Caused by low Concentration of ADP," ASAIO Journal 2000, pp. 593-695.

(Continued)

*Primary Examiner* — Tri T Ton
(74) *Attorney, Agent, or Firm* — Thorpe North & Western LLP

(57) ABSTRACT

A method of evaluating a property of a physiological fluid suspension comprises measuring a value of the property of a liquid portion of the physiological fluid suspension via light scattering, and comparing the measured value with a reference value to evaluate the property of the liquid portion of the physiological fluid suspension.

19 Claims, 4 Drawing Sheets

U.S. PATENT DOCUMENTS

| | | | |
|---|---|---|---|
| 6,043,871 | A | 3/2000 | Solen et al. |
| 6,200,587 | B1 | 3/2001 | Soe et al. |
| 6,673,622 | B1 | 1/2004 | Jina |
| 6,773,923 | B2 | 8/2004 | Patzke |
| 7,037,428 | B1 | 5/2006 | Robinson et al. |
| 7,045,601 | B2 | 5/2006 | Metzner et al. |
| 7,262,059 | B2 | 8/2007 | Zheng et al. |
| 7,393,690 | B2 | 7/2008 | Sukavaneshvar et al. |
| 2003/0096423 | A1 | 5/2003 | Ryan et al. |
| 2004/0065143 | A1 | 4/2004 | Husher |
| 2004/0166551 | A1 | 8/2004 | Moulds et al. |
| 2005/0169968 | A1 | 8/2005 | Elmaleh et al. |
| 2005/0196748 | A1 | 9/2005 | Ericson |
| 2005/0272161 | A1 | 12/2005 | Nichols et al. |
| 2006/0269978 | A1 | 11/2006 | Haworth et al. |
| 2008/0267940 | A1 | 10/2008 | Mohammed et al. |
| 2009/0155832 | A1* | 6/2009 | Lo et al. .......................... 435/29 |

FOREIGN PATENT DOCUMENTS

| | | |
|---|---|---|
| WO | WO 97/29792 | 8/1997 |
| WO | WO 2006/086201 | 8/2006 |

OTHER PUBLICATIONS

Xia et al., "Aggregation Efficiency of Activated Normal of Fixed Platelets in a Simple Shear Field: Effect of Shear and Fibrinogen Occupancy," Biophysical Journal, vol. 55, Jun. 1994, pp. 2190-2201.

Zheng et al., "The Light-Scattering Whole Blood Aggregometer," Arch Pathol lab med, vol. 122, Oct. 1998, 99. 880-886.

Solen et al., "Light-scattering Instrument to Detect Thromboemboli in Blood," Journal of Biomedical Optics, Jan. 2003, vol. 8 No. 1, pp. 70-79.

Ozaki et al., "Detection of Platelet Aggregates with a Particle Counting Method Using Light Scattering," Analytical Biochemistry 218 (1994), pp. 281-294.

Sukavaneshvar et al., "Enhancement of Stent-Induced Thromboembolism by Residual Stenoses: Contribution of Hemodynamics," Annals of Biomedical Engineering, vol. 28, 2000, pp. 182-193.

U.S. Appl. No. 12/214,544, filed Jun. 18, 2008, Sivaprasad Sukavaneshvar.

http://www.erols.com/chronlog Feb. 21, 1998.

"Critical Evaluation of Platelet Aggregation in Whole Human Blood", Riess H., 1985.

"Size Distribution Measurements of Microaggregates in Stored Blood", Reynolds, L., 1979.

"Thrombotic Events on Grafted Polyacrylanide-Silastic Surfaces as Studied in a Baboon", Hoffman, A, 1981.

"Characterization of Blood Microemboli Associated With Ex Vivo Left Ventricular Assist Devices in a Bovine Model", Solen, K., 1989.

"Markers of Thromboembloization in a Bovine Ex Vivo Left Ventricular Assist Device Model", Solen, K., 1994.

"Aggregation of Blood Platelets by Adenosine Diphosphate and Its Reversal", Born, G., 1962.

Alston, Autologous fibrioniogen pruification and concentration for use in fibrin sealant, PhD theisis from Brigham Young University, 2005.

* cited by examiner

US 8,289,514 B2

SYSTEMS FOR MEASURING PROPERTIES OF A PHYSIOLOGICAL FLUID SUSPENSION

This application claims the benefit of U.S. Provisional Application No. 61/068,354, filed Mar. 5, 2008.

FIELD OF THE INVENTION

The present invention relates generally to methods and apparatuses for measuring fluid properties, such as biological, physical or chemical properties of a fluid suspension. More particularly, in one embodiment, the present invention relates to methods and apparatuses for measuring blood clotting function or related properties of a fluid suspension.

BACKGROUND OF THE INVENTION

People who suffer from cardiac or vascular diseases and patients that have undergone surgical procedures are at risk of developing blood clots that may result in life-threatening clinical conditions. Such people are often treated with blood-thinning anticoagulants and/or antiplatelet drugs. However, the amount of anticoagulant or antiplatelet agent(s) in the bloodstream must be maintained at the proper level; too little may result in unwanted clotting while too much can result in hemorrhaging. As a result, routine coagulation screening tests have been developed in order to evaluate the coagulation of blood, plasma, or other blood fractions.

Blood clotting is a complex process involving multiple initiators, activators, enzymes, and modulators where polymerization of fibrinogen ultimately leads to the formation of fibrin, which is a central constituent of a clot. Conventionally, the propensity or ability for blood to clot has been measured by determining the time taken for a sample of plasma or blood to clot. Clot formation may be detected visually, by observing the formation of fibrin, or by automated testing methods, such as photo-optical detection or changes in viscosity.

While such tests have proved useful to some extent, they suffer from a number of problems. For example, conventional test systems can be very expensive to operate and often require specialized instrumentation. Also, conventional test systems can be difficult to standardize and are often affected by abnormal conditions present in the blood being tested. Many conventional systems also only work well within narrow ranges of the clotting response being tested.

Thus, it would be desirable to provide a rapid and comprehensive method for assessment of the clotting activity of a fluid suspension that is quick, accurate, and cost effective.

SUMMARY OF THE INVENTION

In accordance with one embodiment of the invention, a method of evaluating a property of a liquid portion of a physiological fluid suspension is provided, including; measuring a value of the property of the liquid portion of the physiological fluid suspension via light scattering; and comparing the measured value with a reference value to evaluate the property of the liquid portion of the physiological fluid suspension.

In accordance with another aspect of the invention, a method of evaluating the ability of a fluid to clot is provided, including: inducing flow of a fluid within a fluid container by exerting a force on the fluid; measuring a baseline flow rate of the fluid; inducing clotting within the fluid; measuring a secondary flow rate of the fluid after inducing clotting and while the fluid is acted upon by the force; and determining a degree of clotting in the fluid based on a difference between the baseline flow rate and the secondary flow rate of the fluid.

In accordance with another aspect of the invention, a method for determining a degree of clotting in a fluid suspension is provided, including inducing flow of the fluid suspension by exerting a force on the fluid; inducing platelet aggregation in the fluid suspension; determining a baseline fluid flow rate of the fluid suspension after platelet aggregation using platelet aggregates as optical markers; inducing clotting in the fluid suspension; determining a secondary fluid flow rate of the fluid suspension after clotting and while the fluid is acted upon by the force using platelet aggregates as optical markers; and determining an extent of clotting of the fluid suspension based on the difference between the secondary fluid flow rate and the baseline fluid flow rate.

In accordance with another aspect of the invention, a system for determining a degree of clotting within a fluid is provided, including a container for retaining a fluid therein. A flow inducing system can be operable to induce flow of the fluid retained within the container. A clot inducing system can be operable to induce clotting in the fluid retained within the container. A fluid flow measurement system can be operable to measure at least: a baseline fluid flow rate of the fluid retained in the container; and a secondary flow rate of the fluid retained in the container. A degree of clotting of the fluid can be determined by comparing the baseline flow rate of the fluid and the secondary flow rate of the fluid.

In accordance with another aspect of the invention, a method is provided for determining the clotting of a fluid based on a rate at which differential light scattering reaches a reference value or a time interval required for the differential light scattering to reach a reference value, without capturing a baseline measurement in the sample.

Additional features and advantages of the invention will be apparent from the detailed description which follows, taken in conjunction with the accompanying drawings, which together illustrate, by way of example, features of the invention.

Figure 1:
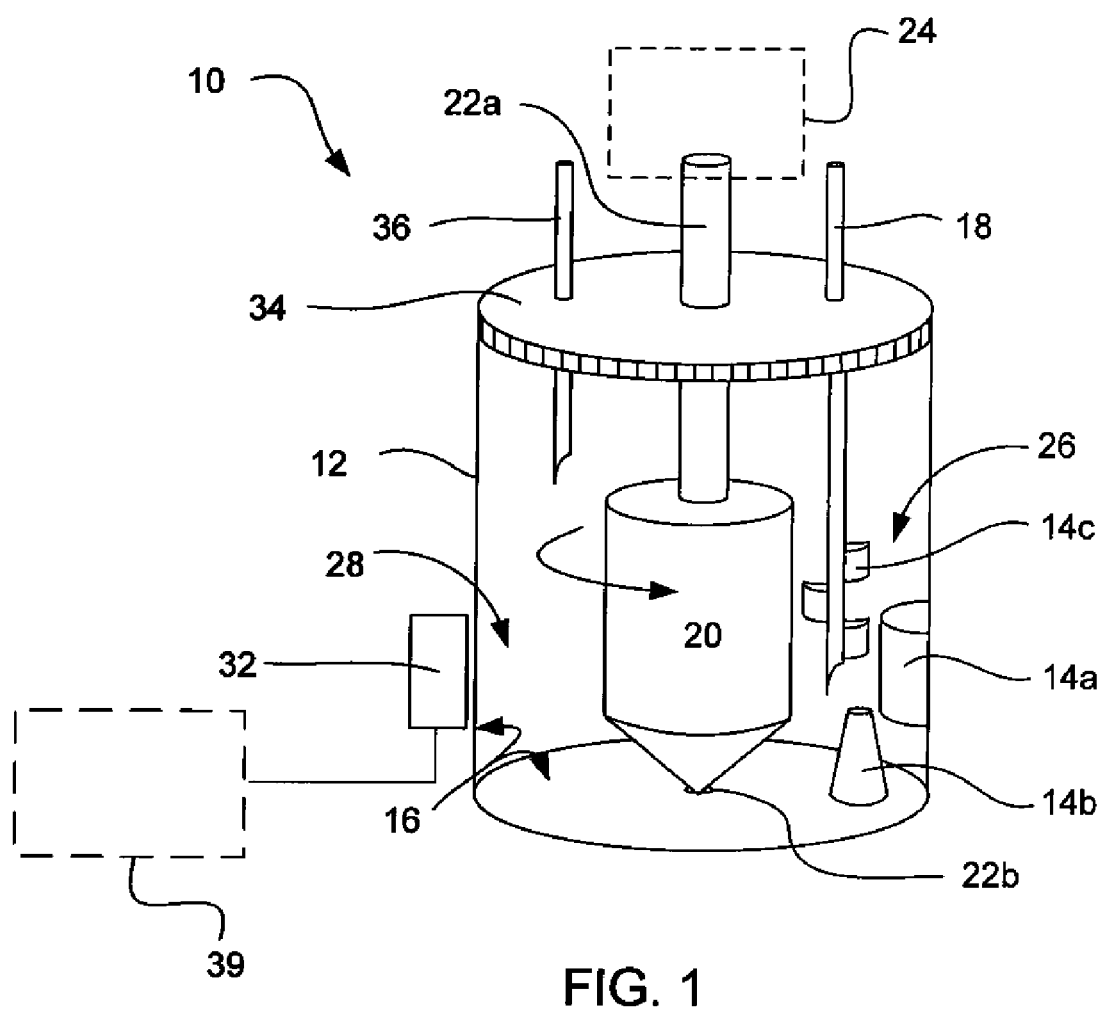
FIG. 1 is a perspective view of an exemplary fluid property measurement system in accordance with an embodiment of the present invention.

The drawings are intended to illustrate exemplary embodiments of the present invention and are not intended to be unnecessarily limiting. As such, departure may be had in dimensions, materials, and features while still failing within the scope of the invention.

DETAILED DESCRIPTION OF THE PREFERRED EMBODIMENT(S)

Reference will now be made to the exemplary embodiments illustrated in the drawings, and specific language will be used herein to describe the same. It will nevertheless be understood that no limitation of the scope of the invention is thereby intended. Alterations and further modifications of the inventive features illustrated herein, and additional applications of the principles of the inventions as illustrated herein, which would occur to one skilled in the relevant art and having possession of this disclosure, are to be considered within the scope of the invention.

In describing and claiming the present invention, the following terminology will be used.

The singular forms "a," "an," and "the" include plural referents unless the context clearly dictates otherwise. Thus, for example, reference to "a rotor" can include reference to one or more of such structures, and reference to "a clotting agent" can include reference to one or more of such clotting agents.

As used herein, "fluid" refers to a flowable composition and can include liquid, gas, suspended solid, or other flowable mass. Fluids can be in the form of suspensions, emulsions, solutions, mixtures, colloids, or the like.

As used herein, "mixing" refers to disturbed flow or separated flow of a fluid. In one embodiment, the addition of a chemical stimulus can be accompanied by mixing in order to facilitate distribution of the stimulus sufficient to affect the bulk properties of the fluid. As used herein, mixing does not include mixing that is merely the result of intermolecular, intercellular, or structural forces exerted within a fluid under substantially streamlined flow, or which is solely the result of diffusion due to concentration gradients.

As used herein, "streamlined" refers to a fluid flow state that is more streamlined than is present in a mixing region acting on the same fluid. Additionally, a streamlined flow is capable of providing fluid flow dynamics such that at least a substantially accurate measurement can be taken, such as by use of a light scattering device or other fluid property measuring device. Further, streamlined flow typically refers to minimally disturbed flow that can be predominantly laminar, including arcuate flow in case of a cylindrical container. Such flow is suitable for testing using methods such as light scattering, etc. Although a common definition of the term "streamlined" can define a path or paths characterized by a moving particle in a fluid such that the tangent to the path at every point is in the direction of the velocity flow, the term as used herein is intended to be broader in scope to include flow that is minimally disturbed such that more accurate readings using fluid measuring equipment can be used, e.g., light scattering particle detection devices.

As used herein, "suspension" is to be understood to refer to a heterogenous fluid containing at least a dispersed phase (e.g., blood cells) and a dispersed medium (e.g. blood plasma). As the term "suspension" is used herein, blood plasma is itself a suspension: and it can also form a portion (e.g., the dispersed medium) of a suspension (e.g., whole blood). In some cases, differential light scattering is used to measure properties of suspensions through time as the suspensions exist in various stages. As such, measurement of a property of a suspension may result in a null value of one of the components at a particular stage. In other words, as used herein, a fluid can be referred to as a "suspension" despite the fact that only one of the dispersed phase or the dispersed medium may be detectable at a specific time (it generally being the case that such a suspension has either just changed from a state when both the dispersed phase and the dispersed medium are detectable, or is about to change to such a state).

The suspension can comprise a variety of physiological fluids including, without limitation, blood, blood plasma, whole blood, spinal fluid, semen, mucous, milk, aqueous humor, bile, urine, saliva, sweat, tears, gastric juice, pancreatic juice, serum, protein suspensions, platelet suspensions, red blood cell suspensions, white blood cell suspensions and the like.

As used herein, "differential light scattering" refers to the scattering of signals emanating from two or more entities that may be in and/or outside a fluid, or a liquid portion of a physiological fluid solution.

Concentrations, amounts, and other numerical data can be presented herein in a range format. It is to be understood that such range format is used merely for convenience and brevity and should be interpreted flexibly to include not only the numerical values explicitly recited as the limits of the range, but also to include all the individual numerical values or sub-ranges encompassed within that range as if each numerical value and sub-range is explicitly recited. Further, such an interpretation should apply regardless of the breadth of the range or the characteristic being described.

The present invention provides systems and methods for measuring properties of fluids. A variety of fluids can be suitable for measurement using the present invention. Suitable fluids include, but are not limited to, physiological fluids such as whole blood, platelet suspensions, platelet rich plasma, platelet poor plasma, leukocyte suspensions, plasma, red blood cell suspensions, urine, bile, etc. Additionally, physiologically compatible fluids, such as saline, or immiscible fluids, such as oils (with water based fluids) can be added to a fluid to be measured for a desired purpose. In one embodiment, these or other fluids or particulates can contain exogenous additives such as polymer microbeads or nanoparticles, fibrinogen coated beads, cells, powders, agonists, antagonists, and mixtures or combinations thereof. These additives can facilitate measurement or otherwise affect the fluid so as to improve handling and/or measurement. Some of the following description focuses on using a fluid suspension such as whole blood, plasma and the like, to measure clotting function (or clotting ability) of the fluid suspension. This has been done for convenience, and is only an example of one of the types of fluid that can be used with the present invention.

In accordance with one aspect of the invention, the present invention provides a method of evaluating a property of a liquid portion of a multi-component suspension. The method can include measuring a value of the property of the liquid portion of the suspension via light scattering, then comparing the measured value with a reference value to evaluate the property of the liquid portion of the multi-component suspension. While not so required, the method can be utilized to measure the ability of whole blood or plasma to clot (generally in the presence of some clotting agent introduced during the process to the whole blood or plasma). In some embodiments, the process can be used to detect the clotting ability of the blood by measuring only characteristics of the liquid portion (e.g., plasma portion) of the blood. While the system may utilize non-liquid portions of the blood (e.g., blood cells, platelet aggregates, etc.) to measure the property of the liquid portion, it is only the behavior of the liquid portion that is being evaluated.

In one aspect of the invention, the method can include measuring, via light scattering or a similar technique, a baseline value of the property of the liquid portion of the suspension. A change can be introduced in the multi-component suspension (e.g., a clotting agent can be added to whole blood), after which a light scattering measurement can be taken of a changed value of the property of the liquid portion of the multi-component suspension. A comparison of the changed value of the property of the liquid portion to the baseline value of the property of the liquid portion can be undertaken to determine the value of the property of the multi-component suspension (e.g., to determine the ability of the blood to clot).

In one aspect of the invention, the time elapsed between a fluid in a base condition and in a changed condition can be measured in order to determine a rate of change of the fluid. The rate of change can be either a positive rate of change (e.g., a time it takes a fluid to increase in viscosity or flow rate to a time when the fluid reaches an increased value of viscosity or flow rate); or a negative rate of change (e.g., a time it takes a fluid to decrease in viscosity or flow rate to a time when the fluid reaches a decreased value of viscosity or flow rate). In some cases, a degree of clotting, or a clot strength value, may be measured by a slowing of fluid flow within the system. An exemplary test system is illustrated in FIG. 1 that can be used in accordance with one embodiment of the invention in which the ability of a fluid to clot can be measured. The system can include a container 12 for retaining a fluid (not shown) therein. The container can generally be operable to recirculate fluid and can be shaped so as to allow fluid to circulate within the container recursively. While not so required, in one aspect, the fluid flows unidirectionally in a substantially circular pattern, however a variety of recirculating flows can be used in accordance with embodiments of the present invention.

In one aspect of the invention, the fluid container 12 can provide for an essentially batch process wherein fluid is introduced into the container either in a single charge or incrementally. Generally, however, the flow of the fluid inside the container will follow a recirculating path through the same region or regions.

The fluid container 12 can be comprised of a variety of materials that are compatible with a chosen fluid to be mixed and a property measured. Additionally, the fluid container 12 can be configured to facilitate measurement of various properties using known methods. For example, in one aspect of the invention, the fluid container is intended for use with a light scattering measurement system. In this instance, the container 12 can be formed from transparent or translucent materials that permit passage of light through the container walls and into the fluid. Many plastics can be used, including, but not limited to, polycarbonates, polyacrylates, polystyrenes, polyvinylchlorides, polyurethanes, and other polymeric materials.

Glass or its variants such as silicated glass can also be a suitable material for the container, depending upon the fluid being tested and the duration of exposure to the fluid. Typically, when the fluid is a blood component-containing fluid, the fluid container can be formed of a relatively small size that is capable of handling very small volumes of fluid. In one aspect of the present invention, the fluid container has a volume of less than 10 ml, while an internal volume of less than about 1 ml can be sufficient. One current embodiment of the present invention has an internal fluid capacity from about 0.05 ml to 0.5 ml. Generally, the fluid containers can have a volume from about 0.02 ml to about 30 ml.

The system 10 can include a flow inducing system, shown by example as including motor or drive assembly 24 operably coupled to a rotor 20. Rotor 20 has been found to minimize or limit destruction of the fluid or its properties when inducing flow of the fluid. In addition to the rotor, other flow inducing components can be utilized, including a stir bar (not shown), forced flow device (not shown), or an external drive (not shown). These and other methods of inducing flow can also be suitable for use in the present invention, as these can not adversely affect the fluid properties. Suitable flow inducing components will induce flow in a blood component-containing fluid and will not damage aggregates, destroy coagulated masses, or otherwise adversely affect the blood components, such as by causing significant hemolysis.

In the embodiment shown, the rotor 20 is a cylindrical body having a conical portion at a bottom end. The rotor can be rotated and secured using shaft 22$a$ and cavity 22$b$ system. The shaft 22$a$ can be coupled to a constant or variable speed motor (a component of the motor or drive assembly 24) that can be used to adjust the rotational speed as desired.

In the example shown, the fluid container 12 can include a mixing region 26 configured for substantial mixing of the fluid in the fluid container. The mixing region 26 can be a region within the container 12 in which the fluid is mixed, and which is separate from a measuring or streamlined flow region 28. The mixing that can occur in the mixing region 26 can be turbulent or gentler in action, but should be sufficient to substantially mix or homogenize the composition of the entire fluid. Thus, the measurement of fluid properties in the separate measuring region 28 can be representative of the bulk properties of the fluid and not be overly subject to localized fluid phenomena.

The separation of mixing region 26 and measuring region 28 allows for increased control of the fluid flow environment, and improves the ability to prevent damage to the fluid. The mixing region 26 can be produced using a variety of disruption members 14$a$, 14$b$, and/or 14$c$, such as a stationary obstruction, movable obstruction, rotating mixer, vagile object, or combinations thereof. These disruption members can cause a local disruption or turbulence in the streamline flow of the fluid sufficient to mix the fluid.

In one aspect of the present invention, the disruption members 14$a$, 14$b$, 14$c$ protrude from an inside surface 16 of the fluid container 12. The disruption members 14$a$, 14$b$, 14$c$ can be molded as an integral part of the container, or can be separately formed members. Additionally, the disruption members 14$a$, 14$b$, 14$c$ can be attached to the inner surface 16 in a permanent or removable manner. FIG. 1 shows disruption members 14$a$ and 14$c$ as stationary obstructions affixed to the inner surface 16 of side walls of the fluid container 12. Disruption member 14$c$ is also shown wherein baffles are affixed to an elongated rod member 18. The rod member 18 can be a rotating or fixed shaft, or a hollow tube inlet for introducing fluid or other material into the fluid container. Disruption member 14$b$ can be a stationary obstruction affixed to the inner surface 16 bottom of the fluid container 12.

One or more disruption member 14$a$, 14$b$, 14$c$ can affect mixing in the mixing region 26 in the vicinity of the one or more member 14$a$, 14$b$, 14$c$. Three different disrupting members are shown for exemplary purposes only. One disrupting member is typically sufficient to provide disturbed flow, or even turbulent flow, though more than one can be present at or near the mixing region 26 in some embodiments.

The mixing region 26 can vary in size depending on such variables as the fluid flow velocity approaching the disruption members, fluid viscosity, and the particular shape of the disruption member(s). Often a single disruption member and mixing region is sufficient to produce substantial mixing of the fluid. However, as shown in FIG. 1, multiple mixing regions can be present.

In one embodiment, the surfaces that contact the fluid, i.e., rotor 20 and/or inside surface 16, can be configured to be highly compatible with the introduced fluid, and can also be configured to avoid contamination of the fluid and/or deterioration of the surfaces. For example, the fluid container 12, if made for use with whole blood or plasma, can be made of materials that are generally compatible with blood or plasma. Additionally, it may be desirable for aggregates or clots not to adhere to surfaces within the apparatus or system 10, such as the inner surface 16 of the fluid container 12, the rotor 20, the disruption member(s) 14a, 14b, 14c, or other parts of the apparatus. This can be accomplished by using smooth geometries in the apparatus and/or coatings, such as lubricious, hydrophilic, or hydrophobic coatings on the apparatus components. Such coatings, if used, can increase biocompatibility and/or decrease friction and associated adherence to the coated surfaces. Coatings suitable for use in the present invention can include, but are not limited to, hydrophilic, hydrophobic, lubricious, heparin, carbon-diamond, or ceramic coatings. Alternately, it may be desirable to induce clots to adhere to the surfaces within the apparatus. This can be accomplished by using corrugated or rough geometries or coatings that promote adherence.

In addition to the above components, the fluid container 12 can include a cap 34 to retain the fluid within the fluid container 12 and prevent spillage of the contents. The cap 34 can be made of a material that has similar properties to that of the fluid container 12, e.g. sufficient mechanical strength and compatibility with the fluid. The cap 34 can also be formed as an integral part of the fluid container 12. Optionally, the cap can also contain self-sealing ports through which the fluid and/or additional material, such as clotting agents, can be introduced. In one embodiment, fluid can be introduced through an inlet line 36, or through depositing the fluid into the fluid container 12 prior to securing the cap 34. The inlet line 36 can be configured as shown in FIG. 1, or can be an aperture (not shown) in the wall of the fluid container. Optionally, the inlet can be in an opening on a disruption member, as shown in with respect to disruption member 14c (inlet line 18). In an alternative embodiment, a volume of fluid in excess of what is desired can be dispensed into the container, such that when the cap 34 is placed on the fluid container 12, a portion of the medium overflows out of the container 12 to achieve the desired volume of medium inside the container 12. Alternatively, the fluid container 12 can be pre-evacuated for a specific volume so that the fluid can be drawn into the container 12 by vacuum for the desired volume.

A fluid flow (or other fluid property) measurement system 32 can be operatively associated with the measuring region 28. The property measurement system can be a light scattering measurement system, or another known light scattering device, optical device, ultrasound, electromagnetic device, or mechanical device. The fluid property measuring device can be used to measure fluid flow rate of the fluid. In one aspect of the invention, a degree of clotting of the fluid can be determined using the fluid flow measurement system.

In a typical scenario, a multi-component suspension fluid (e.g., whole blood or plasma, not shown) can be introduced into the container 12 and flow of the fluid can be induced with the fluid flow inducing system (e.g., rotor 20), and light scattering can be measured. A clot inducing material (not shown) can be introduced into the fluid (or can be predispensed in the container) to cause clotting within the fluid. After at least some degree of clotting has taken place, clotting of the fluid can be determined by the fluid property measuring system 32. A comparator 39 can then determine, based, for example, on the difference in light scattering between the baseline and the clotted fluid, a degree of clotting that has taken place in fluid.

Generally, as clotting occurs within the fluid, the viscosity of the fluid will increase (e.g., the fluid will become more thick), and the fluid will flow at a lower velocity than the baseline flow rate. The difference between the higher velocity (baseline) and lower velocity (secondary) fluid flow can be used to determine an extent of clotting in the fluid suspension. The light scattering signals from red cells, or white cells, or platelets, or cell aggregates, or exogenous particulates, or features can be indicative of the velocity and change in velocity as the fluid thickens.

In those embodiments in which it is applicable, clotting can be induced in the fluid in a variety of manners. As discussed above, a clotting agent (e.g., material) can be added to the fluid to induce clotting. In addition, physical stresses can be imparted to fluid to induce clotting within the fluid. For example, shear stresses can be imparted to (or on, or in) as the fluid flows adjacent a rotor or other physical body within the system. The shear stresses imparted to the fluid can result in clotting within the fluid. Thus, in one example, shear stresses can be used as agonists in the system.

The present invention can measure fluid properties in a variety of manners. Numerous fluid flow measurement devices are available, including non-invasive devices such as optical devices, and more invasive devices (not shown) that may require placement in the fluid stream to determine the fluid properties. In one embodiment, the fluid properties measurement system includes light scattering measurement device that detects various markers within the fluid suspension. The markers used can be produced as a byproduct of clotting, or the markers can be introduced into the fluid suspension for the purpose of determination of flow rate. A variety of such suitable markers are well known to those of ordinary skill in the art.

In one aspect of the invention, platelet aggregates can be utilized as light scattering markers within the fluid suspension. In an exemplary application, a fluid suspension (e.g., blood or plasma) can be introduced into the container 12, and platelet aggregation can be induced in the fluid suspension. After aggregation has occurred, a baseline light scattering measurement of the fluid suspension can be made. Clotting can then be induced in the fluid suspension, after which another light scattering measurement can be made. A degree of clotting can be evaluated based on the difference in light scattering between the baseline and clotted fluid. The presence of the aggregates can be beneficial in providing light scattering marker to enhance the accuracy of the fluid property measurement under relevant conditions. This aspect of the invention can be advantageous in that the marker used to determine fluid property can be related to the clotting function of the blood or plasma.

In one aspect of the invention, red blood cells can be utilized as light scattering markers within the fluid suspension. In an exemplary application, a fluid suspension (e.g., blood or plasma) can be introduced into the container 12, and a baseline light scattering measurement of the fluid suspension can be made. Clotting can then be induced in the fluid suspension, after which another light scattering measurement can be made. A degree of clotting can be evaluated based on the difference in light scattering between the baseline and the clotted fluid. The presence of the red cells can be beneficial in providing light scattering marker to enhance the accuracy of the fluid property measurement under relevant conditions. This aspect of the invention can be advantageous in that the marker used to determine fluid property can be independent of the clotting function of the blood or plasma.

To aid in accurately measuring the fluid flow rate of the fluid suspension, a measuring region or streamlined flow region 28 can be provided that is distinct from the mixing region 26. The measuring region 28 can be configured for providing substantially streamlined flow of the fluid within the fluid container 12.

In another aspect of the present invention, streamlined flow can be induced in a fluid by an external drive, such as by rotating the fluid container while holding a rotor stationary (or rotating at a different rate or direction), or by otherwise moving the fluid container to cause fluid flow in a desired manner.

Figure 2A:
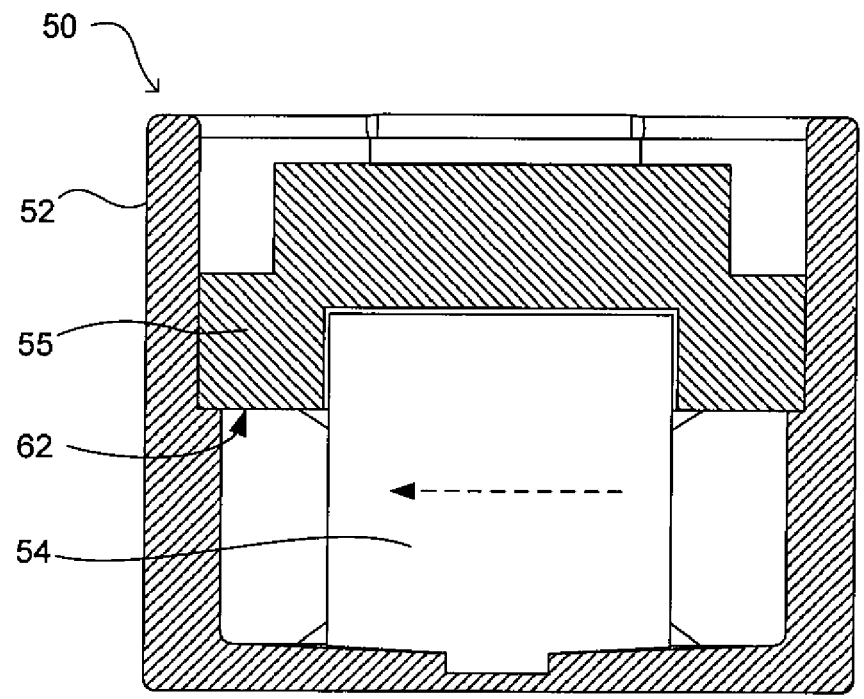
FIG. 2A is a cross-sectional view of an alternative fluid property measurement system having a stenotic baffle system in accordance with an embodiment of the present invention.

FIG. 2A illustrates a fluid property measurement system 50 in accordance with another embodiment of the invention. In this aspect, a fluid container 52 can include a fluid movement device such as a rotor 54 positioned within the fluid container. The fluid movement device can be configured to produce flow of fluid within the container along a desired fluid flow path, e.g., causing circumferential recirculation. In the case of FIG. 2A, the fluid flow path is an annular recirculating flow, caused by the rotor spinning within the fluid container. A cap 55 can be configured to fit over the rotor within the fluid container as shown to provide a seal and to prevent loss or contamination of the contents during use. The fluid container and cap can optionally include threaded surfaces to allow mating of the two pieces. Alternatively, the cap can be secured via an interference fitting, latch, snap, adhesive, seal, welding, ultrasonic welding, laser welding, and/or other similar mechanism.

Figure 2B:
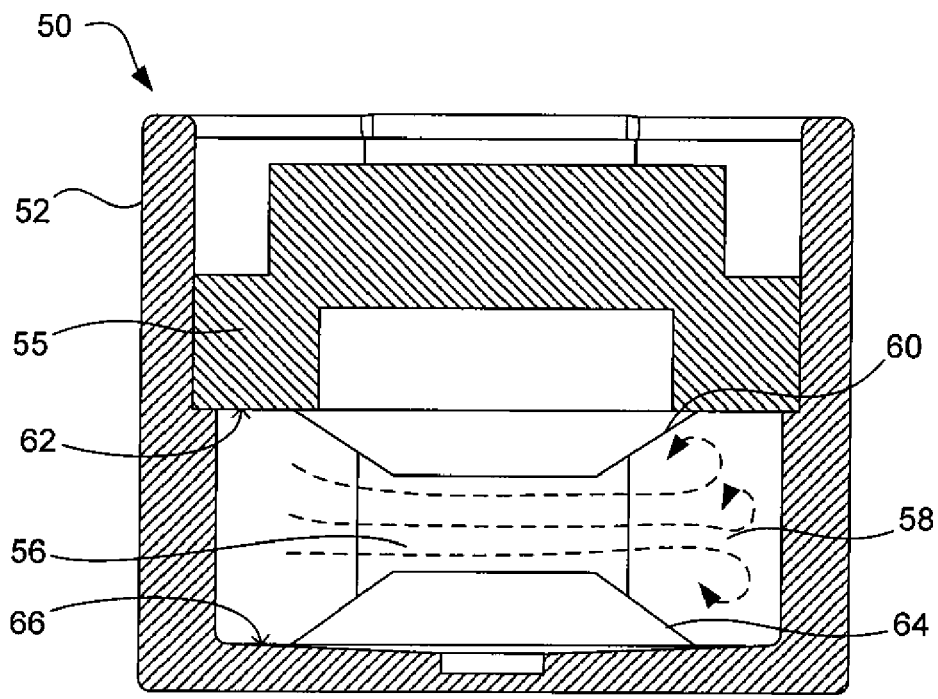
FIG. 2B is a cross-sectional view of the embodiment shown in FIG. 2A having the rotor removed.

The measuring region can be a constricted region where fluid flow passes through a volume having a smaller cross-sectional area than neighboring volumes along the fluid flow path. FIG. 2B is a cross-sectional view of the system 50 of FIG. 2A having the rotor removed. A constricted region 56 can be formed which generates a region of streamlined flow within the constricted region, shown generally by three flow lines 57. Thus, the constricted region can cause the fluid to increase in velocity over a portion of the fluid flow path. An increase in fluid velocity can improve particulate measurement results based on light scattering. The constriction can also facilitate fluid dynamic focusing that concentrates particulates to be measured in the detection region. In addition, increased fluid velocity can reduce agglomeration or blockage of the fluid flow path. Such methods can benefit from increased resolution and decreased signal-to-noise ratio as fluid flow is increased. As the fluid exits the constricted region, at least some mixing occurs as the fluid expands outside of the constricted region into a mixing region 58. Advantageously, the constricted region and subsequent expansion that occurs in the mixing region thus acts to provide streamlined flow and mixing using a single feature, e.g., stenotic baffle. Such expansion mixing also achieves some of the purposes of the present invention by reducing damage to blood components and other fragile materials.

The constricted region shown in FIG. 2B is a stenotic baffle system including a top baffle 60, which in this embodiment is positioned on the cap 55 to form an upper streamlined flow surface for the constricted region 56. A bottom baffle 64 can also be formed along a lower inner surface 66 of the fluid container to form a lower streamlined flow surface of the constricted region. In the embodiment shown in FIG. 2B, though the top baffle is positioned on the cap, the top baffle can alternatively be attached to or formed as in integral part of the fluid container. It should be noted that though not necessary, a secondary disruption member such as those shown and described in connection with FIG. 1 can also be used in conjunction with the stenotic baffle embodiment described herein. The secondary disruption member can be positioned anywhere except in the constricted region (as it would disrupt the streamlined flow), but is preferably positioned at or near the mixing region 58 following the streamlined stenotic baffle.

Figure 2C:
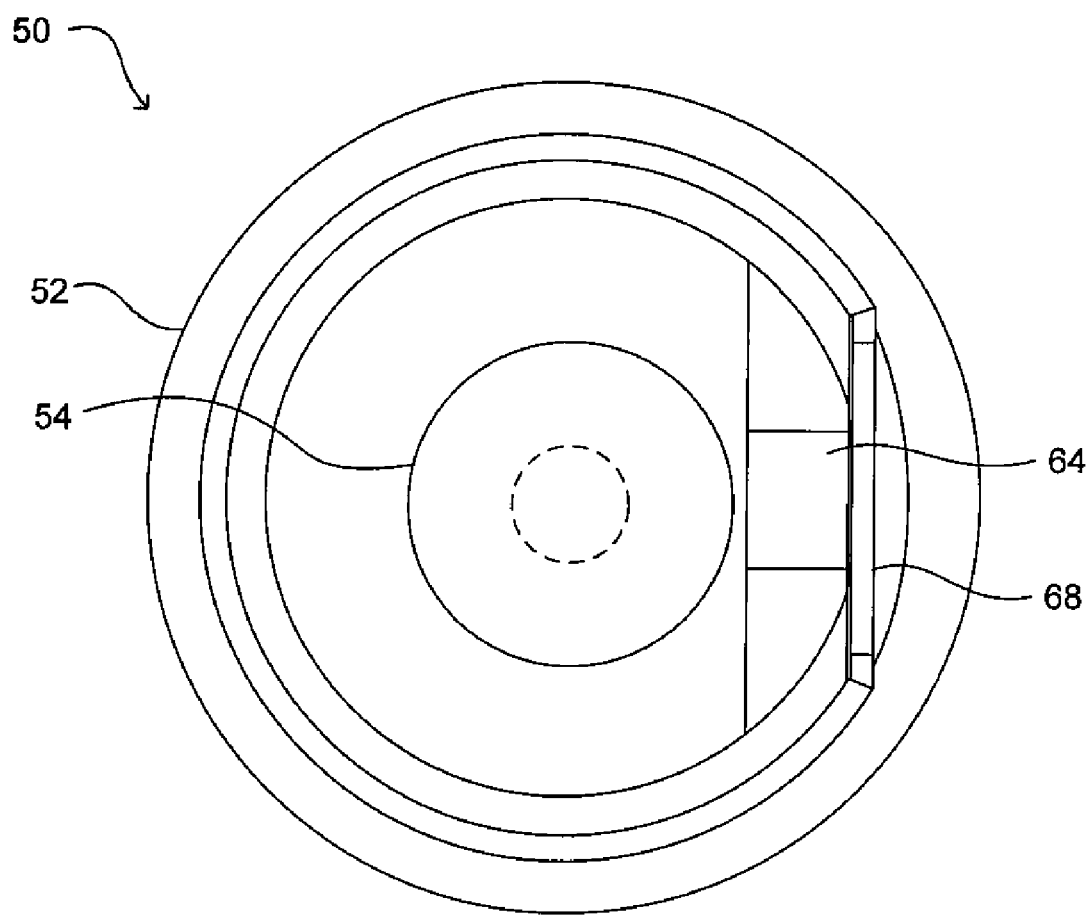
FIG. 2C is a top view of the embodiment shown in FIG. 2A having the cap removed.

FIG. 2C is a top view of the fluid property measurement system 50 having the cap removed. From this perspective, the bottom baffle 64 can be seen having a width which covers nearly the entire fluid path width. In one embodiment, the distance between the rotor and the baffles can be carefully chosen in order prevent damage to fluid (or solid components carried by a fluid) that passes therebetween while also maximizing the constricting affect of the stenotic baffle system. Typically, the stenotic baffles system can have a width from about 50% to about 95%, and preferably about 75% to about 95% of the shortest distance between the inner wall and the rotor. Further, the bottom baffle can be oriented adjacent a light transparent window 68 which is also placed along at least a portion of the constricted region. The constricted region, or measuring region, can allow the light transparent window to be used for measurement of aggregation or other particulates via light scattering devices or other property measurement devices as described above. The light transparent window can alternatively be translucent, as long as the wavelength of light used can pass through the window functionally. The constricted region can alternatively be formed by using a single stenotic baffle. In yet another aspect of the present invention, the constricted region can be formed having conically fluted entrance and exit points. In one embodiment, the baffle or baffle assembly design can produce three dimensional velocity vectors that result in radial, circumferential, and/or vertical mixing.

Although introduction of a single clotting agent is usually sufficient, several agents that jointly or cooperatively induce clotting can be introduced either simultaneously or sequentially. In keeping with the present invention, there are several mechanisms by which the clotting agent can be introduced into the fluid suspension. Chemical and/or biological stimuli (e.g., clotting agents) can be injected into the fluid by a pipette, a needle, or other types of injection devices. Alternatively, the stimulus can be pre-dispensed onto an interior surface (e.g. by coating or as a dried or lyophilized powder) within the container such as a disruption member, baffle, rotor, or inner surface of the container. In keeping with the present invention, the stimulus can also be dispensed into the fluid container prior to the introduction of the fluid into the container, in which case, a baseline fluid flow rate can be quickly established before the onset of the response. In yet another optional embodiment, the stimulus can be introduced into the fluid after placing the fluid into the container.

Figure 3:
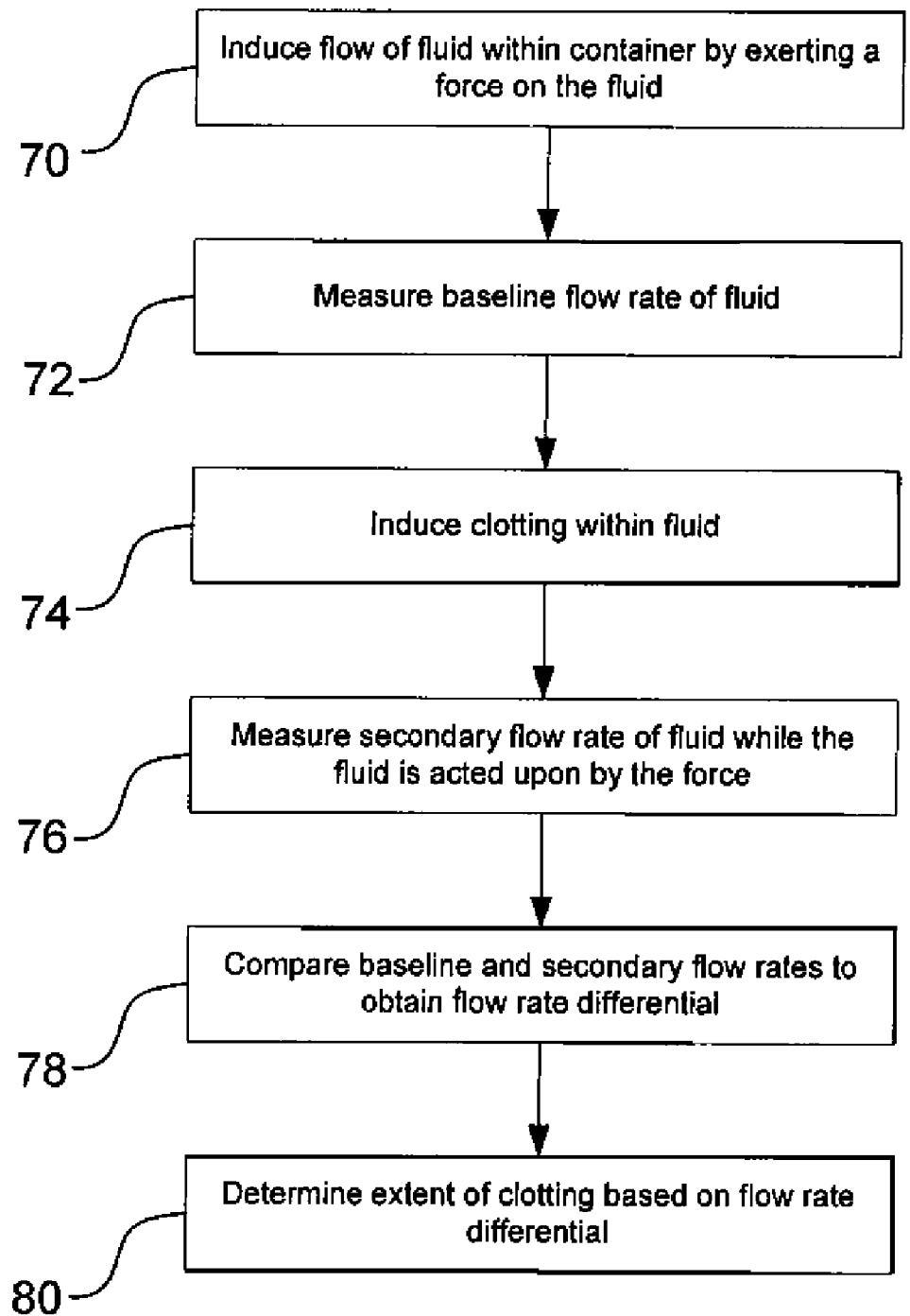
FIG. 3 is a flowchart illustrating processes of an exemplary method in accordance with an embodiment of the present invention.

In addition to the methods and apparatuses discussed above, the present invention also provides a specific method for determining a degree of clotting in a fluid suspension, illustrated in the flowchart of FIG. 3. The method can include inducing, at 70, flow of a fluid within a fluid container. At 72 a baseline light scattering of the fluid can be measured. Inducing clotting within the fluid can be performed at 74, after which light scattering of the fluid can be measured at 76. At 78 a difference in light scattering between the baseline and clotted fluid can be determined. At 80 a degree of clotting in the fluid can be determined based on the difference in light scattering between the baseline and clotted fluid.

The fluid suspension can be selected from the group consisting of whole blood, platelet suspensions, leukocyte suspensions, red blood cell suspensions, blood plasmas, blood plasma components, protein solution, protein suspensions, suspension of modified proteins, suspension of cells, suspension of modified cells, suspension of particulates, and combinations thereof.

Inducing or inhibiting clotting within the fluid can include adding a clotting agent or inhibitor to the fluid. The clotting agent can be selected from the group consisting of calcium salts, thromboplastin, actin, thrombin, silica, diatomaceous earth, kaolin, russel viper venom, ristocetin, clotting factors, and mixtures thereof.

The processes of inducing flow of the fluid, measuring light scattering at baseline and after clotting, and determining the degree of clotting in the fluid can be automated processes performed by an integral testing system.

The above description and examples are intended only to illustrate certain potential uses of this invention. It will be readily understood by those skilled in the art that the present invention is susceptible of a broad utility and applications. Many embodiments and adaptations of the present invention other than those herein described, as well as many variations, modifications, and equivalent arrangements will be apparent from or reasonably suggested by the present invention and the forgoing description thereof without departing from the substance or scope of the present invention.

Accordingly, while the present invention has been described herein in detail in relation to its preferred embodiment, it is to be understood that this disclosure is only illustrative and exemplary of the present invention and is made merely for purpose of providing a full and enabling disclosure of the invention. The forgoing disclosure is not intended or to be construed to limit the present invention or otherwise to exclude any such other embodiment, adaptations, variations, modifications and equivalent arrangements, the present invention being limited only by the claims appended hereto and the equivalents thereof.

What is claimed is:

1. A method of evaluating a property of a liquid portion of a physiological fluid suspension, comprising:
   establishing a baseline value for the property of the liquid portion of the physiological fluid suspension;
   inducing a change in the physiological fluid suspension;
   measuring a changed value for the property of the physiological fluid suspension; and
   comparing the baseline value with the changed value to evaluate the property of the liquid portion,
   wherein at least one of the baseline value and the changed value are measured when the physiological fluid suspension is in motion, and wherein the motion is recirculated flow.

2. The method of claim 1, at least one of the steps of i) establishing the baseline value, and measuring the changed value, is carried out via light scattering.

3. The method of claim 1, further comprising calculating a rate of change of the property of the liquid portion of the physiological fluid suspension.

4. The method of claim 3, wherein calculating the rate of change of the property of the liquid portion is based upon a time elapsed in reaching the changed value of the property.

5. The method of claim 1, wherein the physiological fluid suspension is selected from the group consisting of whole blood, platelet suspensions, leukocyte suspensions, red blood cell suspensions, blood plasmas, blood plasma components, protein solution, protein suspensions, suspension of modified proteins, suspension of cells, suspension of modified cells, suspension of particulates and combinations thereof.

6. The method of claim 2, wherein the physiological fluid suspension includes platelets, and platelet aggregates of the physiological fluid suspension are used as optical markers for the light scattering.

7. The method of claim 2, wherein the physiological fluid suspension includes blood cells, and blood cells of the physiological fluid suspension are used as optical markers for the light scattering.

8. The method of claim 2, wherein the physiological fluid suspension includes extraneous particulates added thereto, and the extraneous particulates added to the physiological fluid suspension are used as optical markers for the light scattering.

9. The method of claim 8, wherein the extraneous particulates include microspheres or nanoparticles.

10. The method of claim 2, wherein one or more features external to the physiological fluid suspension is used as an optical markers for the light scattering.

11. The method of claim 1, wherein both the baseline value and the changed value are measured when the physiological fluid suspension is in motion.

12. The method of claim 1, wherein the baseline value is established when the fluid is stationary and wherein the changed value is measured when the fluid is in motion.

13. The method of claim 1, wherein the baseline value is measured when the fluid is in motion and wherein the changed value is measured when the fluid is stationary.

14. The method of claim 1, wherein the property to be evaluated is the ability of the physiological fluid suspension to clot.

15. The method of claim 1, wherein the property to be evaluated is a viscosity of the liquid portion of the physiological fluid suspension.

16. The method of claim 1, wherein the property to be evaluated is a turbidity of the liquid portion of the physiological fluid suspension.

17. The method of claim 1, wherein the property to be evaluated is a distribution of constituents in the physiological fluid suspension.

18. The method of claim 1, wherein the property to be evaluated is a color of one or more constituents of the physiological fluid suspension.

19. The method of claim 1, wherein the property to be evaluated is an increase or a decrease in viscosity of the liquid portion of the physiological fluid suspension.

* * * * *